US009011936B2

(12) United States Patent
He et al.

(10) Patent No.: US 9,011,936 B2
(45) Date of Patent: Apr. 21, 2015

(54) **EXTRACT OF *ROSMARINUS OFFICINALIS* L. LEAVES FOR PHARMACEUTICAL APPLICATIONS**

(75) Inventors: Kan He, River Edge, NJ (US); Marc Roller, Morieres les Avignon (FR); Alvin Ibarra, Hoboken, NJ (US); Naisheng Bai, Highland Park, NJ (US); Jacques DiKansky, Avignon (FR)

(73) Assignee: Naturex, S.A., Avignon (FR)

( * ) Notice: Subject to any disclaimer, the term of this patent is extended or adjusted under 35 U.S.C. 154(b) by 593 days.

(21) Appl. No.: 12/580,783

(22) Filed: Oct. 16, 2009

(65) Prior Publication Data

US 2011/0091580 A1 Apr. 21, 2011

(51) Int. Cl.
*A61K 36/53* (2006.01)
*A61K 36/00* (2006.01)

(52) U.S. Cl.
CPC ...................................... *A61K 36/53* (2013.01)

(58) Field of Classification Search
IPC ............................................ A61K 36/53,36/00
See application file for complete search history.

(56) References Cited

U.S. PATENT DOCUMENTS

| | | | |
|---|---|---|---|
| 5,989,558 A * | 11/1999 | Lopes | ........................... 424/745 |
| 6,432,453 B1 | 8/2002 | Krumhar | |
| 7,223,382 B2 | 5/2007 | Sokolinsky et al. | |
| 2003/0049332 A1 | 3/2003 | Greaves et al. | |
| 2009/0099251 A1 | 4/2009 | De Saizieu et al. | |

OTHER PUBLICATIONS

Tzia et al. Extraction Optimization in Food Engineering. CRC Press 2003. p. 304.*
Shabtay et al. Synergistic Antileukemic Activity of Carnosic Acid-Rich Rosemary Extract and the 19-nor Gemini Vitamin D Analogue in a Mouse Model of Systemic Acute Myleoid Leukemia. Oncology. Oct. 14, 2008. pp. 201-214.*
Mazza et al. Functional Foods, Biochemical and Processing Aspects. vol. 2. CRC Press. 2002. 23 Pages.*
International Search Report, PCT/US2010/52925, Feb. 10, 2011.
Bosch et al., "Subcellular Compartmentation of Diterpene Carnosic Acid and its Derivatives in the Leaves of Rosemary", *Plaint Physiology*, vol. 125; pp. 1094-1102 (2001).

\* cited by examiner

*Primary Examiner* — Patricia A Leith
(74) *Attorney, Agent, or Firm* — Matthias Scholl, PC; Matthias Scholl

(57) ABSTRACT

Disclosed are methods of alleviating oxidative stress, regulating blood glucose levels, and controlling pancreatic lipase activity by administering a Rosemary extract. Such methods may be useful to help body weight and body fat, prevent obesity, and treat hyperglycemia, hyperinsulinemia, cardiovascular disease and Type-2 diabetes. Preferred extracts contain 20% or 50% carnosic acid.

11 Claims, 8 Drawing Sheets

EXTRACT OF *ROSMARINUS OFFICINALIS* L. LEAVES FOR PHARMACEUTICAL APPLICATIONS

FIELD OF THE INVENTION

The present invention relates to the use of Rosemary (*Rosmarinus officinalis* L.) extract to regulate blood glucose levels, oxidative stress, and/or pancreatic lipase activity and consequently prevent or treat obesity, hyperglycemia, hyperinsulinemia, Type-2 diabetes, cardiovascular disease and other similar conditions.

BACKGROUND OF THE INVENTION

Type-2 diabetes is a chronic metabolic disorder due to a combination of insufficient pancreatic insulin production and/or insulin resistance (IR). The most prominent clinical feature is hyperglycemia characterized by an abnormally high level of glucose in the blood. Hypertension, hyperlipidemia, hyperinsulinemia, and atherosclerosis are often associated with diabetes (Dey et al, 2002, *Altern. Med. Rev.* 7, 45-58). Hyperglycemia can cause oxidative stress which is ultimately responsible for the development of chronic diabetes complications (Ziegler et al, 2004, *Diabetes Care* 27, 2178-83; Evans et al, 2002, *Endoc. Rev.* 23, 599-622). Type-2 diabetes usually begins as IR, and obesity is a known high risk factor for developing IR (Ferrannini et al, 1997, *J. Clin. Invest.* 100, 1166-73). The main biochemical markers of IR include glucose intolerance, dyslipidaemia, and hyperinsulinaemia (Peter et al, 2003, *J. Clin. Pharm. Ther.* 28, 167-74). Therefore, regulation of blood glucose, control of bodyweight and body fat, and attenuation of oxidative stress should be targets in the treatment of Type-2 diabetes.

Rosemary leaf consists of *Rosmarinus officinalis* L. (Family Lamiaceae). It is a culinary spice often used to adjust flavor in cooking and in tea infusion. In folk medicine, Rosemary is used as a choleretic, a diuretic, an antispasmodic, a hair-growth stimulator, to treat gastrointestinal symptoms, as well as other uses (Bruneton, J., *Pharmaconosy, Phytochemistry, Medicinal Plants*, Lavoisier Publishing, Paris, 1995, pp 220; Duke, J., *Handbook of Medicinal Herbs*, CRC Press, Boca Raton, 1985, pp 412-413; al-Sereiti et al, 1999, *Indian J. Exp. Biol.* 37, 124-30). Rosemary is well-known as a natural antioxidant and widely applied in food conservation (Etter 2004, *J. Herbs, Spices, Med. Plants,* 11, 121-59; Suhaj 2006, *J. Food Compos. Anal.* 19, 531-7). Such antioxidant properties are also important to human health since overproduction of free radicals in living organisms can damage cellular lipids, proteins, or DNA, which has been implicated in a number of human diseases including diabetes as well as in the aging process (Valko et al 2007, *Int. J. Biochem. Cell Biol.* 39, 44-84).

Reduction in oxidative status is characteristic of patients having either Type-1 or Type-2 diabetes. This condition in diabetics increases lipid peroxidation and glycosilation of proteins, which leads to complications such as retinopathy, nephropathy, and coronary heart disease. Therefore, supplementation with dietary antioxidants may help to counteract the oxidative stress, and prevent the development of these negative conditions (Al-Azzawie et al, 2006, Life Sci. 78, 1371-7).

Several techniques have been developed to determine the antioxidant power of foods products, vegetal extracts, or pure molecules. These methods have been developed by starting from various principles which can be divided into two large categories of techniques based on major mechanisms that intervene in the stabilization of pro-oxidant species by antioxidants. The first method is based on hydrogen transfer from the antioxidant to the oxidant. The second method is based on electron transfer from the antioxidant to the oxidant. The methods based on hydrogen atom transfer measure the capacity of an antioxidant to trap free radicals by giving them a hydrogen atom. The most widely used is the Oxygen Radical Absorbance Capacity (ORAC) method, which measures the capacity of an antioxidant to inhibit oxidants induced by the peroxyl radical and reflects the inhibition induced by the antioxidant in the stages of initiation and/or propagation of oxidation (Cao et al, 1993, *Free Radic. Biol. Med.,* 14, 303-311). The methods based on electron transfer determine the capacity of an antioxidant to transfer an electron from the antioxidant to the oxidant to reduce the oxidant. One of the most well known of these techniques is the Ferric Reducing/Antioxidant Power (FRAP) method, initially developed to measure the reduction power of plasma. It was later adapted and used for foodstuffs, plants and extracts. Its principle relies on the antioxidant's capacity to reduce Iron III to Iron II in an acidic environment (Pulido et al, 2000, *J. Agric. Food Chem.,* 48, 3396-402).

The oxidation of low-density lipoprotein (LDL) is accepted as an important initial step in the development of atherosclerosis. Indeed, oxidized LDL might be taken up by macrophages to form foam cells, which will combine with leukocytes to become a fatty streak and, later, a fibrous plaque that will protrude into the arterial lumen. If the fibrous plaque ruptures, the thrombi released may occlude vessels and be responsible for adverse coronary syndromes. Recent reports suggest that Rosemary may protect against cardiovascular disease (CVD) (Fuhrman et al, 2000, *Antioxid. Redox. Signal.,* 2, 491-506; Hsieh et al, 2007, *J. Agric. Food Chem.,* 55, 2884-91).

Peroxisome proliferator-activated receptors (PPARs) are nuclear receptors that control many cellular and metabolic processes. These proteins are ligand-activated transcription factors and three isotypes called PPARα, PPARδ and PPARγ have been identified in lower vertebrates and mammals. PPARγ is expressed in the liver, fat, and muscle. The activation of PPARγ increases the transcription of enzymes involved in primary metabolism, leading to lower blood levels of fatty acids and glucose (Evans et al, 2004, *Nat. Med.,* 10, 355-61; Rosen et al 2000, *Genes Dev.,* 14, 1293-1307). PPARγ represents the major target for the glitazone type of drugs currently being used clinically for the treatment of type-2 diabetes. Carnosic acid and carnosol from rosemary and sage have been demonstrated to be activators of the human PPARγ (Rau et al 2006, *Planta Med.,* 72, 881-887).

A major component of dietary fat is triglyceride, or neutral lipid. A triglyceride molecule cannot be directly absorbed across the intestinal mucosa; rather it must be digested into a 2-monoglyceride and two free fatty acids. The enzyme that performs this hydrolysis is pancreatic lipase, which plays an important role in lipid digestion. Orlistat, a strong pancreatic lipase inhibitor, is clinically used for controlling obesity in humans by reducing the amount of fat absorbed from the dietary intake (Scheen et al 1999, *Int. J. Obes.,* 23, Suppl 1, 47-53; Hvizdos et al 1999, *Drugs,* 58, 743-760; Krempf et al, 2003, *Int. J. Obes. Relat Metab. Disord.,* 27, 591-7).

It was found that methanol extract of sage, carnosic acid, and its derivatives had the capacity to inhibit pancreatic lipase (Ninomiya et al, 2004, *Bioorg. Med. Chem. Lett.,* 14, 1943-6). Research showed that carnosic acid and carnosol substantially inhibited pancreatic lipase activity. Carnosic acid significantly inhibited triglyceride elevation in olive oil-loaded mice at doses of 5-20 mg/kg. Furthermore, carnosic acid (20 mg/kg/day) reduced the gain of body weight and the accumulation of epididymal fat weight after 14 days in mice fed a high fat diet.

The hypoglycemic effect of R. officinalis was first reported in 1997, in which the boiling water extract of the leaf of Rosemary was infused into normoglycemic and alloxan-induced hyperglycemic mice, and plasma glucose level was then measured. It was found that the glucose levels in both groups were significantly lower than in the control group (Erenmemisoglu et al, 1997, Pharmazie, 52, 645-6). The effect of 50% ethanol extract of Rosemary on the elevation of plasma glucose levels in the streptozotocin (STZ)-induced diabetic mice was examined. It was shown that Rosemary extract inhibited intestinal α-glucosidase activity to reduce carbohydrate digestion and absorption in mice, significantly suppressing an increase in plasma glucose levels after oral administration of maltose or sucrose. The active compound was identified as the flavonoid, luteolin (Koga et al, 2006, *J. Food Sci.*, 71, S507-12). In a recent report, the hypoglycemic effect of the ethanolic extract from the leaves of Rosemary was observed in normoglycaemic and glucose-hyperglycaemic rabbits. In a study of alloxan-induced diabetic rabbits, the extract significantly lowered blood glucose level and increased serum insulin concentration. According to the authors, the antidiabetogenic effect of the rosemary extract was due to its potent antioxidant properties (Bakirel et al, 2008, *J. Ethnopharmacol.*, 116, 64-73).

SUMMARY OF THE INVENTION

The present invention relates to a nutritional composition to increase antioxidative status, maintain a healthy blood sugar level, and prevent/alleviate/treat Type 2 diabetes. The composition can protect an organism from health problems related to an elevated oxidative stress, such as CVD. The composition is Rosemary acetone extract, such as RosemaryPure® PE 20% and RosemaryPure® PE 50%, which are two rosemary extracts standardized to contain 20% and 50% carnosic acid, respectively (Naturex, Inc.). Such compositions can be prepared by extracting the leaves of *Rosmarinus officinalis* with acetone and purifying through an acid-base procedure to enhance content of carnosic acid and carnosol according to the U.S. Pat. No. 5,859,293 (PCT WO96/34534). This invention also provides a composition having antioxidant capacity which can be used to alleviate oxidative stress-induced Type-2 diabetes and prevent the oxidation of LDL. The present invention provides a composition containing high content of active ingredients carnosic acid and carnosol, which activate peroxisome proliferator-activated receptor (PPARγ) to increase insulin sensitivity and decrease plasma glucose levels, which can be used in patients with Type-2 diabetes. This invention provides a composition comprising an active ingredient that inhibits pancreatic lipase activity in vitro to reduce diet fat absorption, which can be used to aid in weight loss and to prevent obesity associated with Type-2 diabetes. The current invention provides a composition promoting insulin sensitivity against hyperinsulinemia, improving glycaemic and insulinaemic responses. The current invention also provides a composition to reduce body weight and body fat.

BRIEF DESCRIPTION OF THE DRAWINGS

Further features, advantages and characteristics of the present invention will become apparent to a person of ordinary skill in the art in view of the following detailed discussion of preferred embodiments of the present invention, made with reference to the drawings annexed, in which.

DETAILED DESCRIPTION OF THE INVENTION

Figure 1:
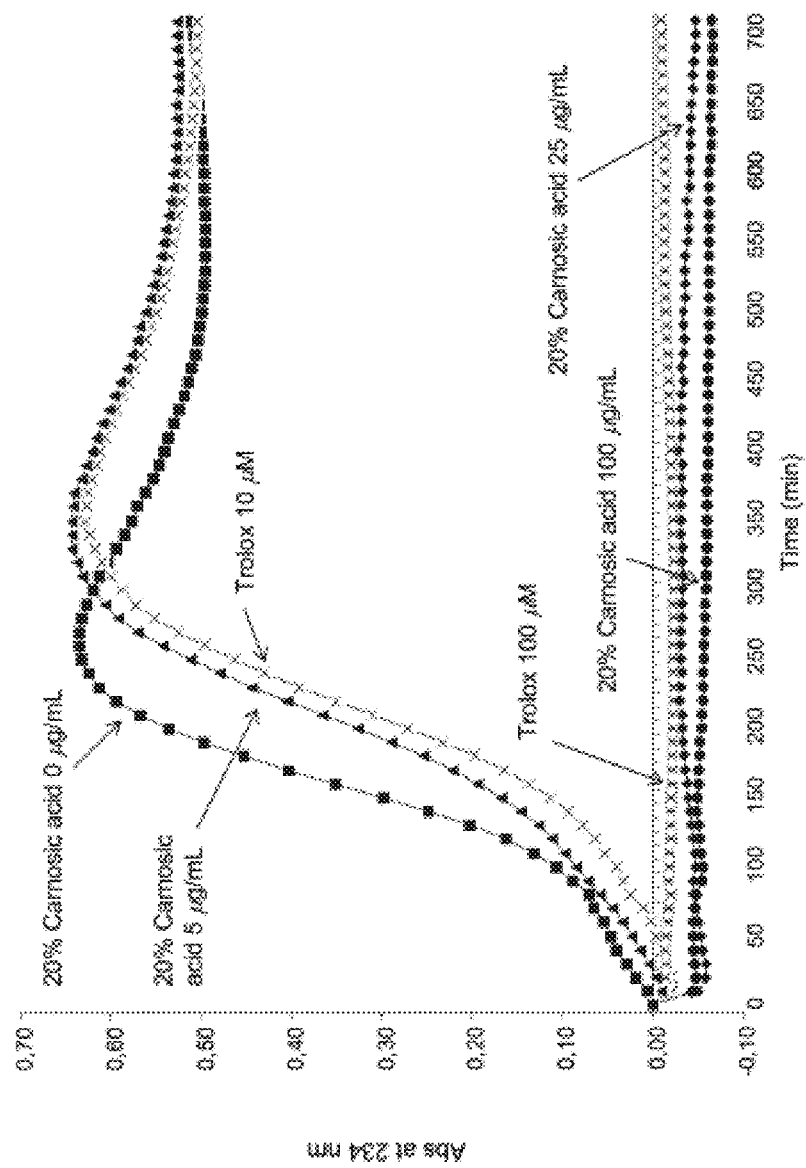
FIG. 1 illustrates a curve for $Cu^{2+}$-induced oxidation LDL with different concentrations (■, 0 μg/mL; ▲, 5 μg/mL; ♦, 25 μg/mL; and ●, 100 μg/mL) of RosemaryPure® PE 20%. Trolox (x, 10 μM; and ✱, 100 μM) was used as the positive control.

The detailed procedure to prepare the composition of Rosemary extract was described in the U.S. Pat. No. 5,859,293 (PCT WO96/34534), which is incorporated herein by reference in its entirety. The procedure is briefly summarized as follows: The Rosemary leaf was extracted with acetone at room temperature. After the extraction was completed, the acetone extract was filtered to separate the solution from Rosemary leaf and concentrated under reduced pressure to make concentrated native extract. At this time, the concentrated extract can be dried directly in a vacuum oven under mild heat to make a powdered extract, RosemaryPure® PE 20%, which is a composition comprising about 15%-30% carnosic acid and 1%-3% carnosol. Or to the concentrated native extract, aqueous sodium carbonate ($NaHCO_3$) was added to dissolve carnosic acid and other organic acids, while base insoluble substances were precipitated out. The solution was filtered to separate from solid, and the filtrate was further concentrated under reduced pressure. Once finishing concentration is achieved, phosphoric acid ($H_3PO_4$) was added and the acid insoluble substances (including carnosic acid, carnosol, and carnosic derivatives) were precipitated from the concentrated solution. Through filtering, the precipitated solid was subsequently separated from liquid and rinsed with water to remove impurities. Last, the solid was dried in a vacuum oven and then milled into powder to make RosemaryPure®

PE 50% which is a composition containing about 40-65% carnosic acid, 2-10% carnosol, and 2-10% 12-O-methylcarnosic acid.

In another embodiment of the invention, the Rosemary extract has antioxidant power on ORAC and FRAP.

In another embodiment of the invention, Rosemary extract protects low density lipoprotein from oxidation. Therefore, the Rosemary extract is able to avoid the formation of atherosclerosis caused by the oxidation of LDL, thus reducing the risk of cardiovascular disease.

In another embodiment of the invention, Rosemary extract, rich in carnosic acid and carnosol, activates the peroxisome proliferator activated receptor gamma (PPARγ) in a dose dependent manner. This property of Rosemary extract further provides an improvement in insulin sensitivity, and a regulation of blood glucose. This effect is especially desirable for individuals with hyperglycemia and diabetes.

In another embodiment of the invention, Rosemary extract is able to inhibit the activity of the pancreatic lipase. Therefore, the ingestion of Rosemary extract consequently reduces the absorption of triglycerides in the organism. Therefore, individuals ingesting Rosemary extract as a complement of their normal diet are expected to reduce the absorption of lipids, and to reduce the accumulation of fat in the body.

In another embodiment of the invention, when male C57BL/6J mice are fed with a high-fat diet, they develop obesity, hyperglycemia, and hyperinsulinemia. Administration of an effective amount of Rosemary extract can significantly decrease the glucose level, decrease plasma insulin level, reduce body fat, and reduce body weight.

EXAMPLES

Example 1

Antioxidant capacities (ORAC and FRAP) of RosemaryPure® PE 20% (RosemaryPure® rosemary extract standardized to contain 20% carnosic acid).

The Oxygen Radical Absorbance Capacity (ORAC) in vitro of RosemaryPure® PE 20% was determined according to an adaptation of the method described by Cao et al. (1993, *Free Radic. Biol. Med.*, 14303-11). ORAC value provides a measure of the scavenging capacity of antioxidants against the peroxyl radical, which is one of the most common reactive oxygen species (ROS) found in the body. $ORAC_{hydro}$ reflects water-soluble antioxidant capacity and the $ORAC_{lipo}$ is the lipid soluble antioxidant capacity. $ORAC_{total}$ is the sum of $ORAC_{hydro}$ and $ORAC_{lipo}$. Trolox, a water-soluble Vitamin E analog, is used as the calibration standard and the ORAC result is expressed as μmol Trolox equivalent per gram.

The ferric reducing/antioxidant power (FRAP) in vitro of RosemaryPure® PE 20% was determined according to an adaptation of the method described by Pulido et al (2000, *J. Agric. Food Chem.*, 48, 3396-402). The FRAP assay offers a putative index of antioxidant potential of biological fluids within the technological reach of every laboratory and researcher interested in oxidative stress and its effects. Two types of calibration curve were made: one with aqueous solutions of known $Fe^{2+}$ concentration, in the range of 100-1,000 μM/L, and another with solutions of known Trolox concentration, in the range of 100-750 μM/L. Extracts were measured in duplicate at three different concentrations after appropriate dilution. In the FRAP assay, reductants in the sample reduce $Fe^{3+}$/tripyridyltriazine complex, present in stoichiometric excess, to the blue colored ferrous form and then measured at 593 nm. The ΔA is proportional to the combined ferric reducing/antioxidant power of the antioxidants in the sample. Results are expressed as μmol of ferric reducing/antioxidant power (FRAP value) per gram of extract and as μM Trolox equivalent/g of extract.

RosemaryPure® PE 20% showed a strong antioxidant capacity in the two tests (Table 1). Its antioxidant capacity is 36% by the $ORAC_{hydro}$ and 64% by the $ORAC_{lipo}$, evidencing a good balance antioxidant power.

TABLE 1

Oxygen radical absorbance capacity (ORAC) and ferric reducing/antioxidant power (FRAP) values of RosemaryPure ® PE 20%.

| | $ORAC_{hydro}$ (μMol Trolox Eq./g) | $ORAC_{lipo}$ (μMol Trolox Eq./g) | $ORAC_{total}$ (μMol Trolox Eq./g) | FRAP (mmol/g) | FRAP (μMol Trolox Eq./g) |
|---|---|---|---|---|---|
| RosemaryPure ® PE 20% | 2,345 | 4,144 | 6,489 | 1.28 | 699 |

Example 2

Inhibition of $Cu^{2+}$-induced LDL oxidation in vitro of RosemaryPure® PE 20%.

LDL was concentrated from the plasma of normolipidemic donors by density gradient ultracentrifugation. Prior to oxidation, LDL was diluted in a phosphate buffered saline (PBS) and dialyzed against PBS at 4° C. to remove EDTA. The protein content was determined and adjusted to obtain 0.125 mg of protein/mL. Next, the oxidation was induced at 30° C. by adding 100 mL of $CuSO_4$ (1.66 mM) with the addition of 0 (control condition), 5, 25, and 100 μg/mL of RosemaryPure® PE 20% or 10 μM and 100 μM of Trolox as the positive control. The amounts of conjugated dienes were measured by determining the increased absorbance at 234 nm at 10 min intervals for a course span of 720 min using a Tecan Ultra Spectrophotometer (Tecan, Austria). Results were expressed as the relative absorbance at 234 nm. The lag phase, oxidation rate, and the maximum quantity of conjugated dienes were calculated. Results are reported as the mean±SD of three trials for each test. Differential between groups was calculated using the Student's t-test (XLSTAT 2008, Addinsoft™, USA), and the statistical significance was set at P<0.05.

The inhibitory activity of RosemaryPure® PE 20% on LDL oxidation mediated by $Cu^{2+}$ has been evaluated. As shown in Table 2 and FIG. 1, it was found to be effective to extend the lag phase, decrease the oxidation speed, and dienes formation in a dose dependant manner. At the lowest concentration tested (5 μg/mL), the carnosic acid extract is able to decrease the oxidation speed by 23.3% (P<0.001). At 25 and 100 μg/mL RosemaryPure® PE 20% showed a complete inhibition of LDL oxidation similar to the inhibition observed with Trolox at 100 μM.

TABLE 2

Overall results for inhibition of LDL Cu$^{2+}$-induced oxidation by RosemaryPure® PE 20%.

| | | Cu$^{2+}$-induced oxidation LDL assay | | |
|---|---|---|---|---|
| | Concentration | Lag phase (min) | Oxidation rate (min$^{-1}$) | Maximum quantity of dienes (nmol/mg of LDL) |
| RosemaryPure® PE 20% | 5 μg/mL | 154.5 ± 10.2 | 76.7 ± 2.4 *** | 101.07 ± 1.2 |
| | 25 μg/mL | NC | NC | NC |
| | 100 μg/mL | NC | NC | NC |
| Trolox | 10 μM | 180 ± 5.2 * | 80.1 ± 4.1 | 99.0 ± 1.2 |
| | 100 μM | NC | NC | NC |

NC = Not calculated since the samples totally inhibits the LDL from oxidation.
P-value =
* P < 0.05;
** P < 0.01;
*** P < 0.001 vs. Cu$^{2+}$-induced oxidation LDL alone (t- test).

Example 3

PPARγ activation of RosemaryPure® PE 20%.

Figure 2:
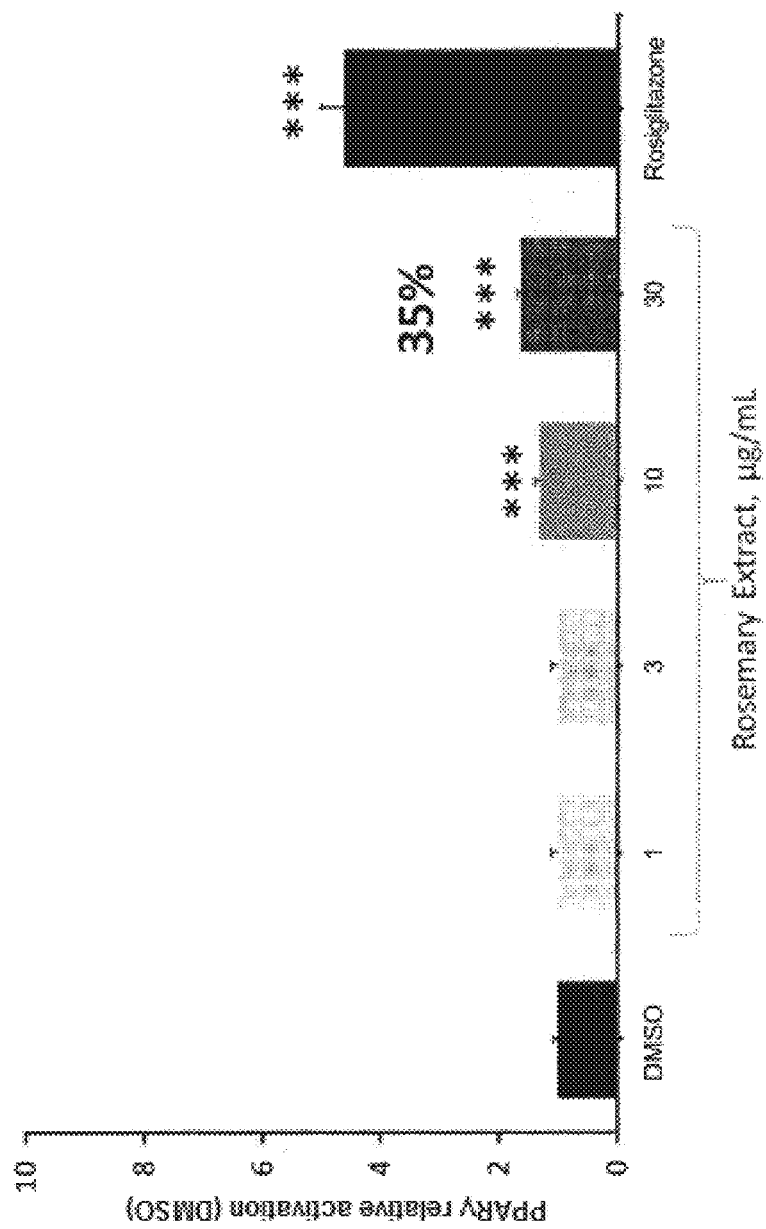
FIG. 2 illustrates Relative activation of the GAL4/PPARγ fusion receptor by RosemaryPure® PE 20% and 100 μM of roziglitazone (positive control) as compared with the effect of DMSO (control condition). Transfected COS-7 cells were treated for 24 h with DMSO, increasing doses of RosemaryPure® PE 20% (1-30 μg/mL), and 100 μM of roziglitazone. Values are mean±SD (n=4). *$P<0.05$, $P<0.01$; *$P<0.001$. Student's t test.

RosemaryPure® PE 20% activated PPARγ in a cell-based assay incubated for 24 h. In this assay, PPARγ was measured using a reporter gene, the luciferase. The cells were previously transferred with a fusion protein GAL4-PPARγ and a DNA construct carrying the gene reporter. The activation of the nuclear receptor by a ligand was then transformed into an increased luminescent signal. The relative activations of PPARγ by RosemaryPure® PE 20% and roziglitazone (positive control) as compared with DMSO (control condition) were calculated from the luminescence signal of luciferase (a reporter gene) obtained from the active compounds after incubation with GAL4/PPARγ receptor transfected cells. First, COS-7 cells (cultured in DMEM+10% FCS) were transiently transfected with a fusion protein GAL4/PPARγ and a DNA construct carrying the luciferase. After transfection, COS-7 cells were incubated for 24 h with 0 μg/mL (control condition), 1, 3, 10, and 30 μg/mL of RosemaryPure® PE 20% or 100 μM of roziglitazone (positive control). DMSO was used as the solvent. After incubation, cells were collected and the luciferase assay was performed. The activation of PPARγ by RosemaryPure® PE 20% and roziglitazone resulted in the expression of luciferase and consequent increment of the luminescent signals, which were measured with a Tecan Ultra Spectrophotometer (Tecan, Austria). Results were expressed as the relative activation of GAL4/PPARα proportional to the luminescent signal emitted as a result of the RosemaryPure® PE 20% and roziglitazone as compared to the luminescent activity of the control (DMSO). Results are reported as the mean±SD of four trials for each test (FIG. 2). Differences between groups were calculated using Student's t-test (XLSTAT 2008, Addinsoft™, USA). FIG. 2 shows the results for PPARγ relative activation. 30 μg/mL of RosemaryPure® PE 20% induces a 23% of PPARγ relative activation as compared to the positive control, 100 μM of roziglitazone.

Example 4

Pancreatic lipase inhibition of RosemaryPure® PE 20%.

Figure 3:
FIG. 3 illustrates relative pancreatic lipase inhibition activity of RosemaryPure® PE 20% as compared to the positive control, 0.1 μg/mL of Orlistat.

RosemaryPure® PE 20% was tested for its relative pancreatic lipase inhibition capacity compared to the positive control, Orlistat (GlaxoSmithKline). In the experiment, aliquots of lipase standard and Rosemarypure® PE 20% at concentrations of 5, 25 and 100 μg/mL were mixed gently and incubated for 5 min at 37° C. Then an activator reagent was added and mixed by gentle inversion and the samples were incubated again for 3 min at 37° C. The recorded rate of increase in absorbance at 550 nm due to the formation of quinine diimine dye was used to determine the pancreatic lipase activity in the samples. FIG. 3 shows the results of this study. 100 μg/mL of RosemaryPure® PE 20% was able to inhibit 61.48% of the pancreatic lipase activity as compared to the positive control, 0.1 μg/mL of Orlistat. In conclusion, RosemaryPure® PE 20% has a potent pancreatic inhibition activity, and may be used to control obesity.

Example 5

Hypoglycemic activity of RosemaryPure® PE 50% on male C57BL/6J mice.

A total of fifty male C57BL/6J mice were divided into three groups: 1) negative control group where 20 male mice were on low-fat diet (LF) with about 10 kcal daily intake; 2) positive control group where 20 mice were fed with high-fat diet (HF) and about 60 kcal was taken daily and due to high-fat feeding, this group of the mice developed obesity, hyperglycemia, and hyperinsulinemia; 3) 0.5% RosemaryPure® PE 50% group where 10 male mice were fed with high-fat diet like those in group 2, but the diet was also mixed with 0.5% of RosemaryPure® PE 50%. Food and fluid intake and body weight were measured weekly. Signs of abnormality and possible toxicity were monitored. Fasting blood glucose level was measured using blood glucose meter at week 5, 8, 10, 12, 14, and 16 and blood was taken from the tail vein. Fasting plasma insulin levels were determined using mouse Elisa kit at week 16, the end of the experiment. A basal data was determined and there was no statistical difference among all the three groups before the experiment.

Figure 4:
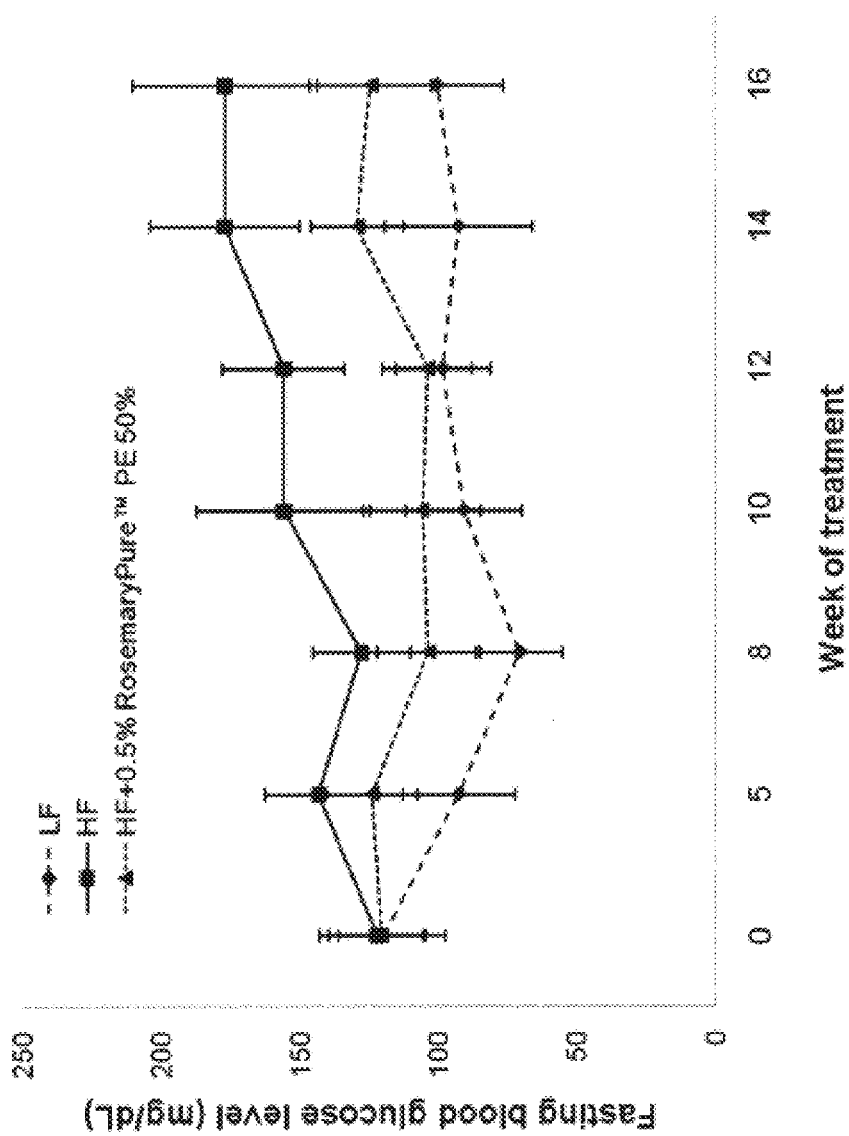
FIG. 4 illustrates fasting blood glucose of low-fat (LF), high-fat (HF), and *Rosmarinus officinalis* leaf extract (HF+RosemaryPure® PE 50%) treated mice during 16-week treatment period.

After a 16-week treatment, mice in the RosemaryPure® PE 50% group showed significantly lower fasting blood glucose levels than the mice in the high-fat control group (p<0.001), which indicated a strong hypoglycemic effect of Rosemary-Pure® PE 50% (FIG. 4).

Example 6

Fasting plasma insulin levels reduction of RosemaryPure® PE 50% on male C57BL/6J mice.

Figure 5:
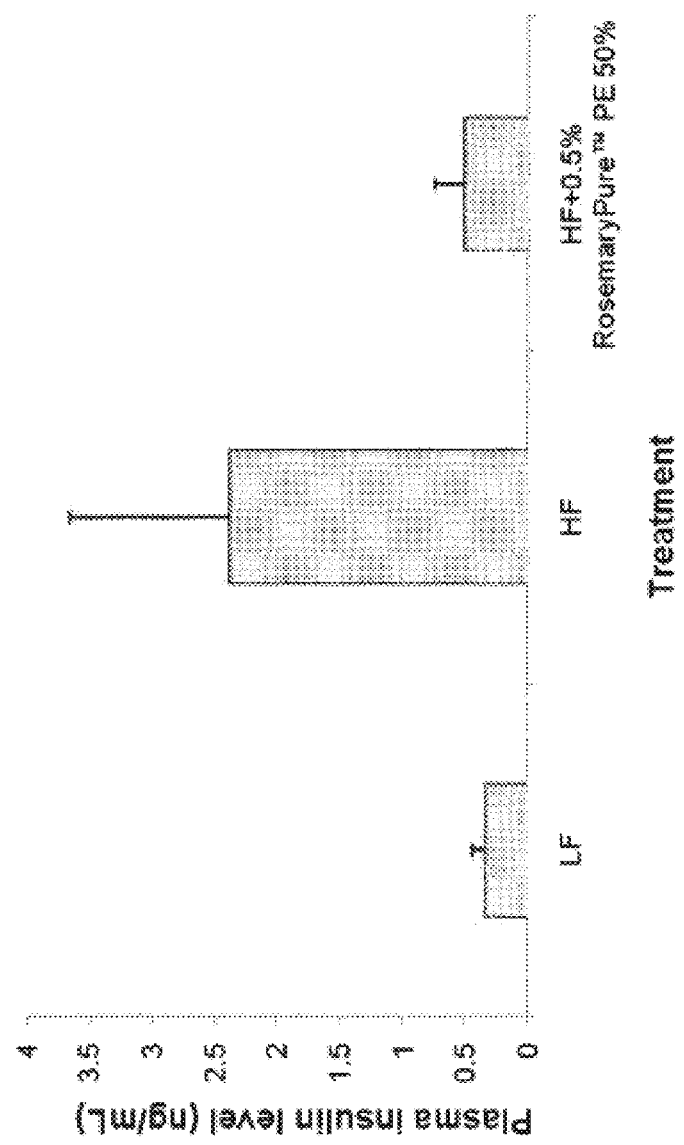
FIG. 5 illustrates fasting plasma insulin levels from individual mouse from the LF (n=10), HF (n=10), and *Rosmarinus officinalis* leaf extract groups (HF+RosemaryFure® PE 50%), respectively.

At the end of the experiment (from Example 5 after 16 weeks), fasting plasma insulin levels were determined using mouse Elisa kit. The RosemaryPure® PE 50% treated mice had significantly lower fasting plasma insulin levels in comparison to that from the high fat control group (p<0.05) (FIG. 5).

Example 7

Bodyweight-reducing activity of RosemaryPure® PE 50% on male C57BL/6J mice.

Figure 6:
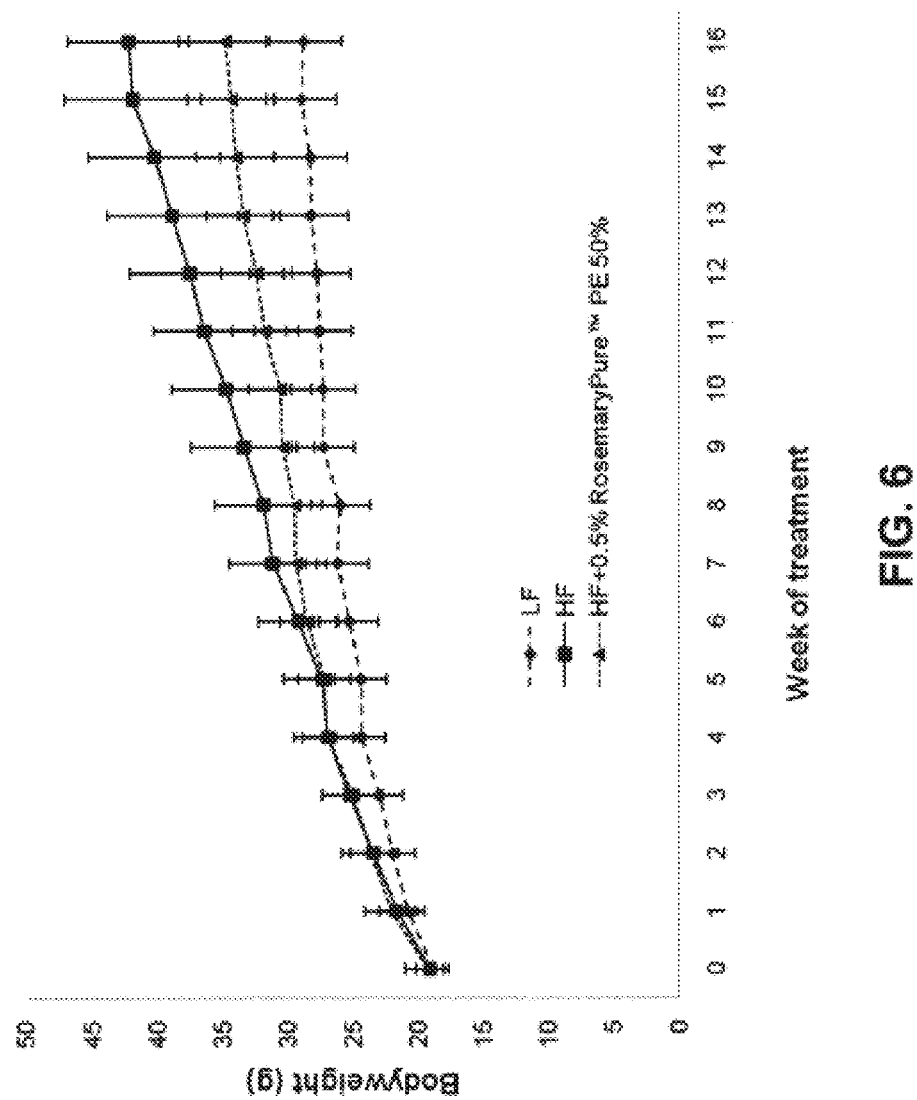
FIG. 6 illustrates average body weight of low-fat (LF), high-fat (HF), and *Rosmarinus officinalis* leaf extract (HF+RosemaryPure® PE 50%) during 16-week treatment period.

Bodyweight of each mouse was measured from the same groups in Example 5. There was no statistical difference among all the three groups of basal bodyweight at the beginning. After 16 week treatment, all the mice in the high-fat treated groups (group 2 and 3) have gained significant bodyweight than those in the low-fat treated group. However, the extent of bodyweight gaining in RosemaryPure® PE 50% group was much lower compared to positive control group, indicating an activity of RosemaryPure® PE 50% on bodyweight control. At the end of the experiment, Rosemary-Pure® PE 50% group showed a significant reduction (54.9%, $p<0.0001$) on bodyweight gain induced by high-fat diet (FIG. 6).

Example 8

Effects of RosemaryPure® PE 50% on omental and retroperitoneal fat in male C57BL/6J mice.

Figure 7:
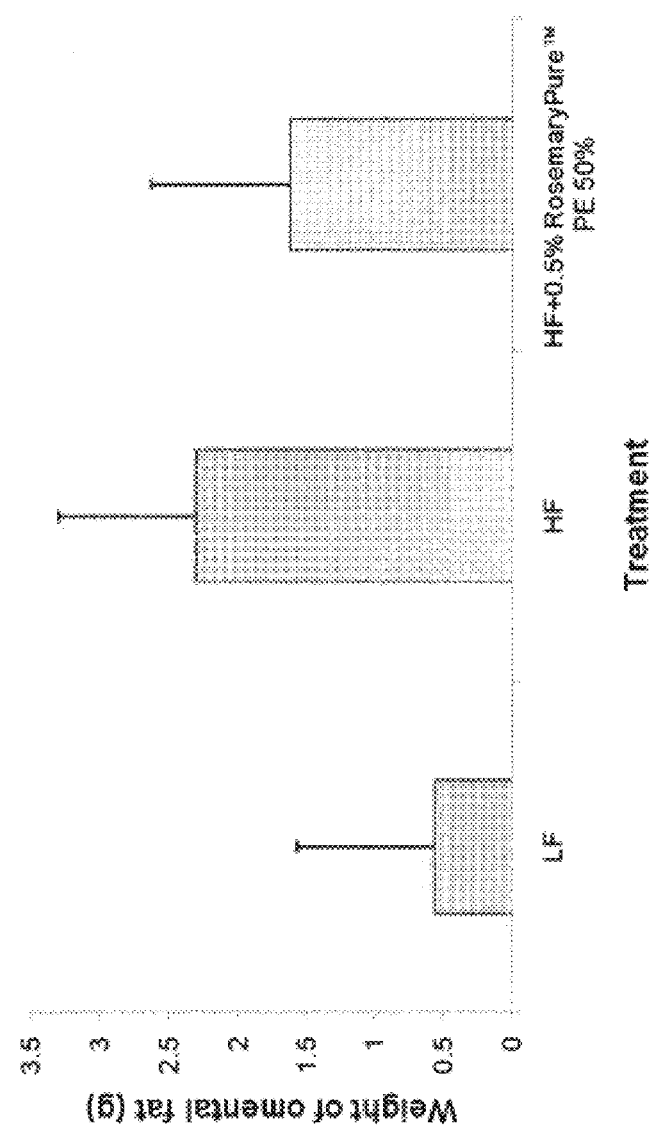
FIG. 7 illustrates weight of the omental fat from individual mice from the LF (n=10), HF (n=10), and *Rosmarinus officinalis* leaf extract groups (HF+RosemaryFure® PE 50%), respectively.
Figure 8:
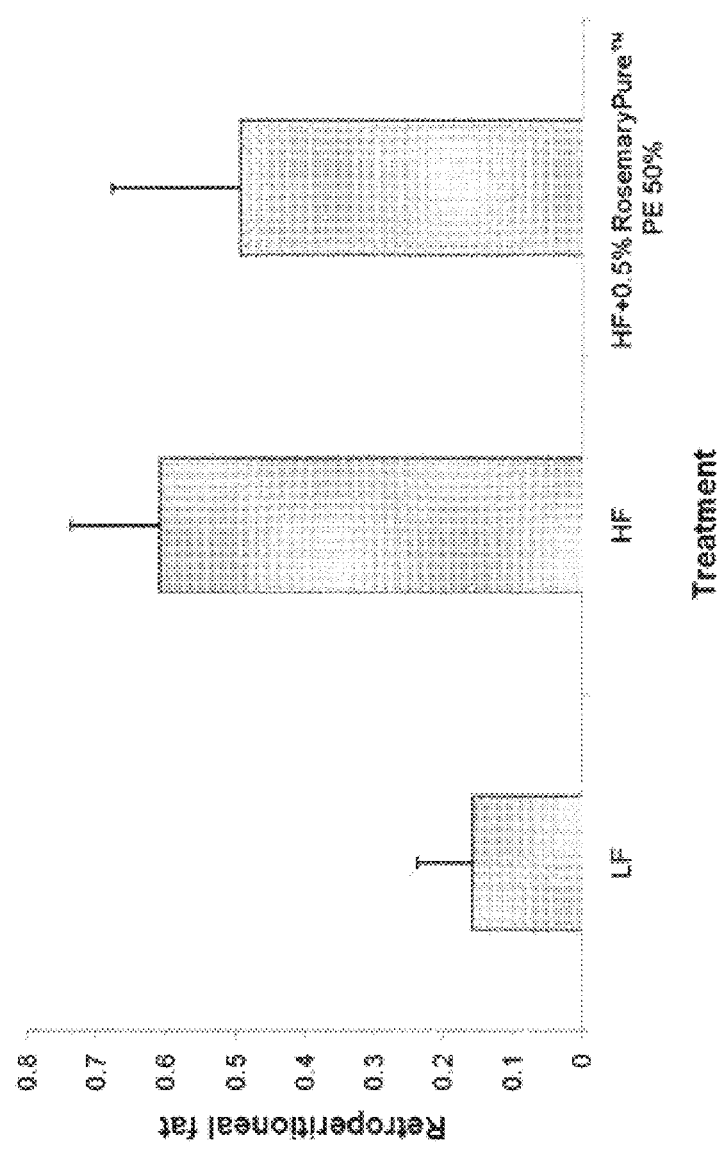
FIG. 8 illustrates weight of the retroperitoneal fat from individual mice from the LF (n=10), HF (n=10), and *Rosmarinus officinalis* leaf extract groups (HF+RosemaryPure® PE 50%), respectively.

After 16-week treatment from Example 5, the mice from all three groups were anesthetized and sacrificed. The omental and retroperitoneal fat from individual mice was collected and weighed. The results showed that the RosemaryPure® PE 50% decreased 38.9% omental fat gain ($p<0.05$) and 25.1% retroperitoneal fat gain, respectively (FIGS. 7 and 8).

One skilled in the art will appreciate that the present invention can be practiced by other than the embodiments disclosed herein, which are provided for purposes of illustration and not limitation.

We claim:

1. A method of decreasing oxidation of low density lipoprotein in a subject in need thereof, the method comprising administering to the subject a composition comprising, by weight of said composition, between about 40% and about 65% carnosic acid, between about 2% and about 10% carnosol, and between about 2% and about 10% 12-O-methylcarnosic acid, in an amount effective to decrease oxidation of low density lipoprotein in the subject.

2. A method of increasing the activity of a peroxisome proliferator-activated receptor in a subject in need thereof, the method comprising administering to the subject a composition comprising, by weight of said composition, between about 40% and about 65% carnosic acid, between about 2% and about 10% carnosol, and between about 2% and about 10% 12-O-methylcarnosic acid, in an amount effective to increase the activity of a peroxisome proliferator-activated receptor in the subject.

3. A method of inhibiting the activity of the pancreatic lipase in a subject in need thereof, the method comprising administering to the subject a composition comprising, by weight of said composition, between about 40% and about 65% carnosic acid, between about 2% and about 10% carnosol, and between about 2% and about 10% 12-O-methylcarnosic acid, in an amount effective to inhibit the activity of the pancreatic lipase in the subject.

4. A method of decreasing fasting blood glucose levels in a subject in need thereof, the method comprising administering to the subject for about 16 weeks a composition comprising, by weight of said composition, between about 40% and about 65% carnosic acid, between about 2% and about 10% carnosol, and between about 2% and about 10% 12-O-methylcarnosic acid, in an amount effective to decrease fasting blood glucose levels in the subject.

5. A method of reducing fasting plasma insulin levels in a subject in need thereof, the method comprising administering to the subject for about 16 weeks a composition comprising, by weight of said composition, between about 40% and about 65% carnosic acid, between about 2% and about 10% carnosol, and between about 2% and about 10% 12-O-methylcarnosic acid, in an amount effective to reduce fasting plasma insulin levels in the subject.

6. A method of reducing bodyweight in a subject in need thereof, the method comprising administering to the subject for about 16 weeks a composition comprising, by weight of said composition, between about 40% and about 65% carnosic acid, between about 2% and about 10% carnosol, and between about 2% and about 10% 12-O-methylcarnosic acid, in an amount effective to reduce bodyweight in the subject.

7. The method of claim 1, wherein the method further comprises preparing said composition by extracting *Rosmarinus officinalis* leaves with acetone; filtering to obtain a first filtrate; adding sodium carbonate to the first filtrate to precipitate base insoluble substances; filtering to obtain a second filtrate; adding phosphoric acid to the second filtrate to precipitate acid insoluble substances and to obtain a solid; separating the solid from liquid phase; drying the solid; and milling the solid to obtain said composition.

8. The method of claim 2, wherein the method further comprises preparing said composition by extracting *Rosmarinus officinalis* leaves with acetone; filtering to obtain a first filtrate; adding sodium carbonate to the first filtrate to precipitate base insoluble substances; filtering to obtain a second filtrate; adding phosphoric acid to the second filtrate to precipitate acid insoluble substances and to obtain a solid; separating the solid from liquid phase; drying the solid; and milling the solid to obtain said composition.

9. The method of claim 3, wherein the method further comprises preparing said composition by extracting *Rosmarinus officinalis* leaves with acetone; filtering to obtain a first filtrate; adding sodium carbonate to the first filtrate to precipitate base insoluble substances; filtering to obtain a second filtrate; adding phosphoric acid to the second filtrate to precipitate acid insoluble substances and to obtain a solid; separating the solid from liquid phase; drying the solid; and milling the solid to obtain said composition.

10. A method of treating hyperglycemia in a subject in need thereof, the method comprising administering to the subject a composition comprising, by weight of said composition, between about 40% and about 65% carnosic acid, between about 2% and about 10% carnosol, and between about 2% and about 10% 12-O-methylcarnosic acid, in an amount effective to treat hyperglycemia in the subject.

11. A method of treating hyperinsulinemia in a subject in need thereof, the method comprising administering to the subject for about 16 weeks a composition comprising, by weight of said composition, between about 40% and about 65% carnosic acid, between about 2% and about 10% carnosol, and between about 2% and about 10% 12-O-methylcarnosic acid, in an amount effective to treat hyperglycemia in the subject.

* * * * *